(12) United States Patent
Novak

(10) Patent No.: US 6,896,664 B2
(45) Date of Patent: May 24, 2005

(54) APPARATUS FOR IRRIGATING A BODY CAVITY WITH A LIQUID

(75) Inventor: Pavel Novak, Stetten (CH)

(73) Assignee: Karl Storz GmbH & Co. KG (DE)

( * ) Notice: Subject to any disclaimer, the term of this patent is extended or adjusted under 35 U.S.C. 154(b) by 91 days.

(21) Appl. No.: 10/323,247

(22) Filed: Dec. 19, 2002

(65) Prior Publication Data

US 2003/0236490 A1 Dec. 25, 2003

(30) Foreign Application Priority Data

Jun. 24, 2002 (EP) .......................... 02014113

(51) Int. Cl.⁷ .............................. A61M 31/00
(52) U.S. Cl. ......................... 604/67; 606/107
(58) Field of Search ................ 604/67, 27–28, 604/30–31, 43, 65; 607/62; 606/107

(56) References Cited

U.S. PATENT DOCUMENTS

| | | | |
|---|---|---|---|
| 3,930,505 A | * | 1/1976 | Wallach ..................... 604/22 |
| 4,261,360 A | | 4/1981 | Perez |
| 4,650,462 A | | 3/1987 | DeSatnick et al. |
| 4,902,277 A | | 2/1990 | Mathies et al. |
| 5,000,733 A | | 3/1991 | Mathies et al. |
| 5,131,823 A | | 7/1992 | Guignard |
| 5,556,378 A | * | 9/1996 | Storz et al. ................. 604/31 |
| 5,685,821 A | | 11/1997 | Pike |
| 6,579,255 B2 | * | 6/2003 | Kadziauskas et al. ........ 604/35 |

FOREIGN PATENT DOCUMENTS

| | | |
|---|---|---|
| DE | 4219890 A1 | 1/1994 |
| EP | 0529902 A2 | 8/1991 |
| EP | 02014113 | 2/2003 |
| WO | WO 00/78372 A1 | 6/2000 |

* cited by examiner

Primary Examiner—Nicholas D. Lucchesi
Assistant Examiner—Catherine S. Williams
(74) Attorney, Agent, or Firm—St. Onge Steward Johnston & Reens LLC

(57) ABSTRACT

An apparatus for irrigating a body cavity with a liquid comprises an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a predetermined nominal pressure and a predetermined nominal flow rate. The control circuit controls the irrigation pump as a function of the nominal flow rate, while it controls the suction pump as a function of the nominal pressure.

16 Claims, 4 Drawing Sheets

APPARATUS FOR IRRIGATING A BODY CAVITY WITH A LIQUID

FIELD OF THE INVENTION

The invention relates to an apparatus for irrigating a body cavity with a liquid, comprising an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a predetermined nominal pressure and a predetermined nominal flow rate. Such an apparatus is known from the document U.S. Pat. No. 4,902,277.

BACKGROUND OF THE INVENTION

An apparatus of the afore-mentioned kind is used for the endoscopic irrigation of body cavities, for example the bladder, the uterus or articular capsules.

The apparatus known from the afore-mentioned document U.S. Pat. No. 4,902,277 can be specially used in arthroscopy in an endoscopic resection of a joint. In this connection, a physiological liquid is pumped by means of an irrigation pump through an irrigation conduit into the joint. The liquid is then drawn off from the joint by means of a suction pump through a suction conduit.

It is desirable during such an endoscopic irrigation of hollow organs that the pressure and the flow rate of the irrigation liquid in the body cavity can be adjusted independently from one another. The flow rate is to be understood as the liquid debit through the body cavity per time unit.

The irrigation pump of the afore-mentioned known apparatus is a displacement pump, which is controlled as a function of the actual pressure in the irrigation conduit or in the body cavity, which is measured by a pressure sensor, in order to maintain a predetermined nominal pressure in the body cavity. The speed of the motor of the irrigation pump is increased or reduced as a function of the actual pressure measured by the pressure sensor, in order to maintain the nominal pressure in the body cavity.

The suction pump of this known apparatus is a displacement pump, too, which is controlled as a function of a predetermined nominal flow rate. In this connection, two flow rates can be adjusted, as a function of which the suction pump is controlled. The suction pump maintains the predetermined flow rate which has been set respectively. The higher nominal flow rate can be set, for example, when a working instrument, for example a resection instrument, is additionally put into operation. The lower nominal flow rate can be set, for example, when the body cavity is just to be irrigated without a working instrument being in operation.

The use of a displacement pump, in particular a roller pump, has the advantage that the flow rate produced by the pump is, to a high degree, proportional to the speed of the displacement pump in particular if the pressure maintained by the irrigation pump is constant.

A disadvantage of this known apparatus comes to light when an obstruction which is, for example, caused by tissue pieces, occurs in the suction conduit. In case of an obstruction in the suction conduit, the actual pressure in the body cavity exceeds the nominal pressure with the result that the irrigation pump of the known apparatus is controlled such that its speed decreases, in order to maintain the nominal pressure. In contrast to that, the suction pump which is adjusted to the predetermined nominal flow rate, works on with an unchanged speed. The result is that the obstruction possibly cannot be drawn off by the suction pump. This can lead to a disturbance and interruption of the irrigation operation and, thereby, of the medical operation.

On the other hand, an apparatus for irrigating a body cavity is known from EP 0 529 902 A2, the irrigation pump of which is a centrifugal pump, which is controlled as a function of a predetermined nominal pressure in the body cavity or in the irrigation conduit, respectively, while the suction pump is a displacement pump in form of a gear pump. Unlike a displacement pump, a centrifugal pump has the characteristic that the produced flow rate is not a single-valued function of the speed of the centrifugal pump, but in addition depends on the actual pressure. With this known apparatus, the flow rate is adjusted by means of a controllable tube-squeezing valve.

This known apparatus has the disadvantage that the irrigation pump, which is designed as a centrifugal pump, is not sealing so that in case that the squeezing valve is not closed and both pumps are not activated, the liquid can unimpededly flow through as a result of the gradient. Another disadvantage of this known apparatus is, as mentioned before, that by using a centrifugal pump as the irrigation pump, the flow rate cannot be preset in exact manner because neither the irrigation pump nor the suction pump allow a simple dependency of the flow rate for example as a function of the speed of the pumps. In this known apparatus, the actual flow rate highly depends on the pressure difference in the system.

It is an object of the invention to provide an apparatus of the afore-mentioned kind by means of which the pressure and the flow rate can be controlled as independently from each other as possible and in a way which differs from the known apparatus.

SUMMARY OF THE INVENTION

According to the invention, this object is achieved with respect to the apparatus mentioned at the outset in that the control circuit controls the irrigation pump as a function of the nominal flow rate, while it controls the suction pump as a function of the nominal pressure.

Unlike the known apparatus, the irrigation pump of the apparatus according to the present invention is not controlled as a function of the nominal pressure, but the predetermined nominal flow rate is adjusted through the irrigation pump. On the other hand, the predetermined nominal pressure is adjusted by means of the suction pump, i.e. the suction pump is controlled to the predetermined nominal pressure. This has the advantage that obstructions in the suction conduit which cause the actual pressure to exceed the nominal pressure, can be drawn off by virtue of an automatically increasing higher suction power of the suction pump. In contrast to that, the apparatus known from U.S. Pat. No. 4,902,277 would only respond to obstructions in the irrigation conduit by reducing the speed of the irrigation pump, whereby, however, the obstruction cannot be removed. Moreover, an obstruction in the irrigation conduit has as good as no relevance in practice, because obstructions are not expected in the fresh irrigation liquid coming from the storage vessel.

In a preferred embodiment, a pressure sensor is associated with the irrigation conduit for determining the actual pressure, and the control circuit controls the suction pump as a function of the actual pressure determined by the pressure sensor for maintaining the nominal pressure.

The advantage herewith is that the nominal pressure can be maintained in a particular exact manner by that the suction power of the suction pump is increased or reduced as a function of the acquired actual pressure in order to maintain the predetermined nominal pressure in the body cavity.

In a further preferred embodiment, the control circuit controls the irrigation pump as a function of the suction power of the suction pump such that the power of the irrigation pump is reduced when the suction power of the suction pump is increased, at least when the suction power of the suction pump exceeds a predetermined threshold value.

This measure is particularly advantageous in terms of the safety of the apparatus for the patient. In case of an obstruction causing the actual pressure in the body cavity to exceed a threshold value and causing the suction pump to strongly increase its suction power accordingly, in order to maintain the predetermined nominal pressure, and in case that the obstruction is such that it cannot be removed despite the increasing suction power, the power of the irrigation pump is decreased or even reduced to zero, in order to avoid a too high pressure in the body cavity and thereby a risk for the patient. Thus, it is avoided that in case of an obstruction which cannot be removed by suction irrigation liquid is still further pumped into the body cavity.

In a further preferred embodiment, the irrigation pump and/or the suction pump are displacement pumps.

The use of displacement pumps has the advantage that controlling these pumps can be done in a simple manner via the speed, wherein another advantage is that the produced debit or flow rate is a substantially single-valued function of the speed of the pump.

In this connection, it is preferred if the irrigation pump is a roller pump or a gear pump.

A roller pump is a displacement pump in which a plurality of rollers are moved along a flexible conduit portion, whereby the liquid conduit is peristaltically narrowed in cross-section. The use of the roller pump is particularly preferred because the flow rate is correlated with the speed of the roller pump in a single-valued manner.

In comparison to that, the use of a gear pump as the irrigation pump has the advantage that the irrigation liquid is fed into the body cavity in a manner substantially free of pulsations.

It is further preferred if the suction pump is a roller pump.

Although a roller pump is not suited to produce a flow free of pulsations, which is, however, not absolutely necessary for the suction pump, the suction pump has the advantage of a single-valued correlation between the flow rate and the speed of the pump and a particularly simple construction.

In alternative embodiments, it can also be preferred if the irrigation pump is a centrifugal pump. In order to advantageously obtain a fixed correlation between the flow rate and the speed, the actual correlation between the flow rate and the speed is first determined for a certain type of a centrifugal pump, and the control circuit then uses the determined correlation for controlling the irrigation pump, in order to adjust or maintain the predetermined nominal flow rate.

In a further preferred embodiment, the control circuit uses the speed of the suction pump as a control signal and controls the irrigation pump as a function of said control signal.

This embodiment is particularly advantageous in case a gear pump is used as the irrigation pump, for which the flow rate is not correlated with the speed of the pump in a single-valued manner, as it usually is the case for a roller pump. The flow rate of a gear pump depends on the suction pressure as well as on the irrigation pressure. For this reason, it is not possible to control the flow rate only by means of the speed of the gear pump, but a regulation is required. Such a regulation of the speed of the irrigation pump can be easily obtained in the afore-mentioned manner as a function of the speed of the suction pump which is preferably configured as a roller pump. In addition, this embodiment is also suited for improving the safety of the apparatus for the patient.

In connection with one of the afore-mentioned embodiments according to which the control circuit controls the irrigation pump as a function of the suction power of the suction pump such that upon an increase of the suction power, at least if the latter exceeds a predetermined threshold value, the power of the irrigation pump is reduced, it is provided in a further preferred embodiment that the control circuit controls the irrigation pump as a function of the speed of the suction pump at least when a flow rate threshold value is exceeded such that the speed of the irrigation pump is reduced when the speed of the suction pump increases.

This embodiment also has the advantage of a control of the irrigation pump which can be realized in a particularly simple manner as a function of the suction power of the suction pump, which results in the desired effect that a danger by a permanent increase of pressure in the body cavity is avoided.

In a further advantageous and preferred embodiment, the control circuit can also control the irrigation pump as a function of the difference between the speeds of the irrigation pump and the suction pump.

In a further preferred embodiment, the control circuit controls the irrigation pump as a function of at least two different nominal flow rates.

With this embodiment, at least two different nominal flow rates can be adjusted through the irrigation pump. In a surgical operation, e.g. an endoscopic operation, the liquid debit through the body cavity can be enhanced in advantageous manner, for example when tissue is dissected in the body cavity so that blood and tissue pieces can be withdrawn in a more efficient manner by virtue of an increased irrigation flow.

In this connection, it is preferred if the control circuit switches over the irrigation pump between the at least two nominal flow rates as a function of the operating condition of a working instrument connected with the control circuit.

The advantage herewith is that the changeover between the at least two nominal flow rates occurs in an automatic manner when the working instrument is switched on or switched off, respectively, so that the physician has not to carry out the changeover herself or himself and is, therefore, not distracted from her or his operative activity.

In a further preferred embodiment, at least two parallel suction conduits lead away from the body cavity, wherein the suction pump is associated with both suction conduits, wherein further one suction conduit is connected with a working instrument, and wherein it can be switched over between both suction conduits as a function of the operating condition of the working instrument.

In this case, the working instrument used for a surgical operation, e.g. a resection instrument, is simultaneously configured as a suction instrument, and upon actuating the working instrument, the liquid and dissected tissue is then drawn off via the working instrument, wherein the changeover between both suction conduits again occurs in an automatic manner without the physician having to carry out the changeover from his or her side.

In a further preferred embodiment, the control circuit determines the difference between the speeds of the suction pump and the irrigation pump.

This embodiment is particularly advantageous in case roller pumps are used as the irrigation pump and the suction pump so that the correlation between the flow rate and the speed is single-valued. In this case, the afore-mentioned embodiment has the advantage that the loss of liquid in the body cavity, which can be caused by liquid entering into the blood stream, can be relatively well-determined by subtraction of the speeds of both pumps.

Further advantages and features will become apparent from the description that follows, and from the attached drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and are explained in more detail in the description which follows. In the drawings.

DETAILED DESCRIPTION OF THE DRAWINGS

Figure 1:
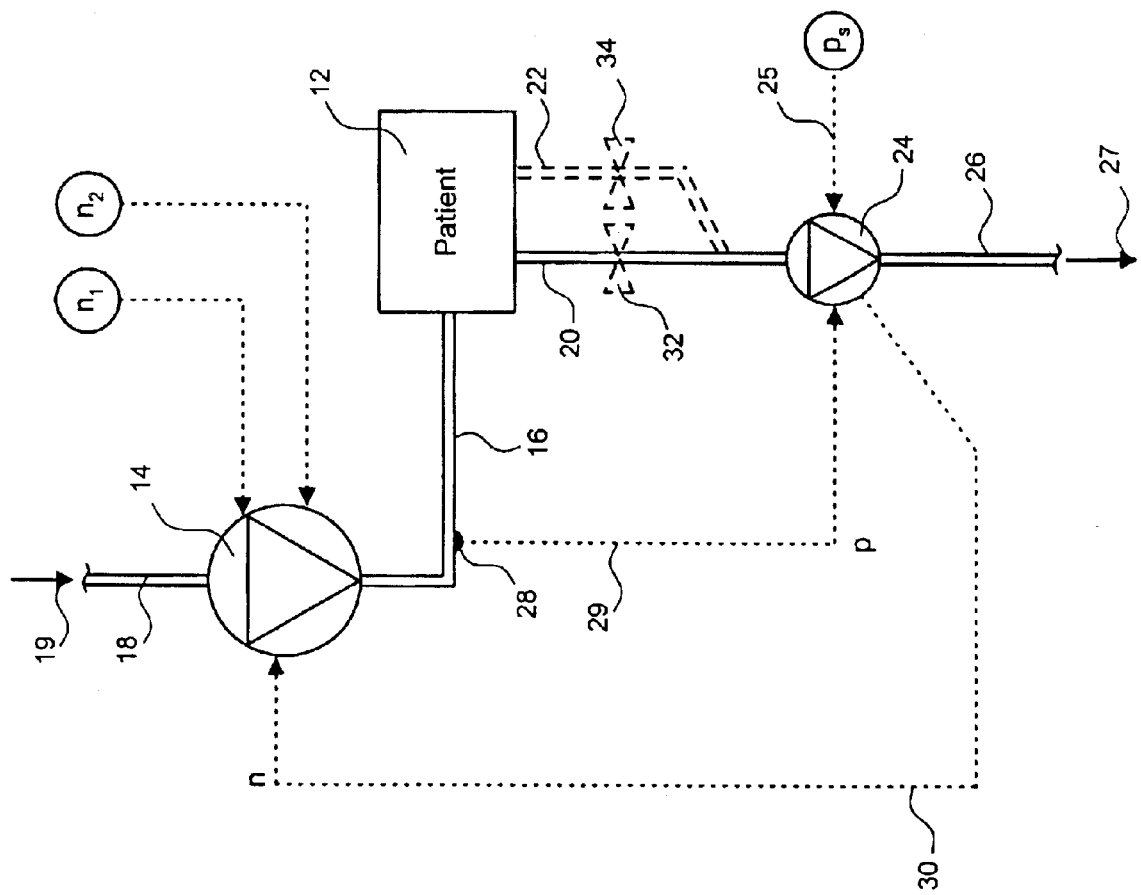
FIG. 1 is a schematic block diagram of an apparatus for irrigating a body cavity according to a first exemplary embodiment.

FIG. 1 schematically shows an apparatus generally labeled with reference numeral 10 for irrigating a body cavity 12 with a liquid. The liquid is a physiological liquid, for example.

Figure 2:
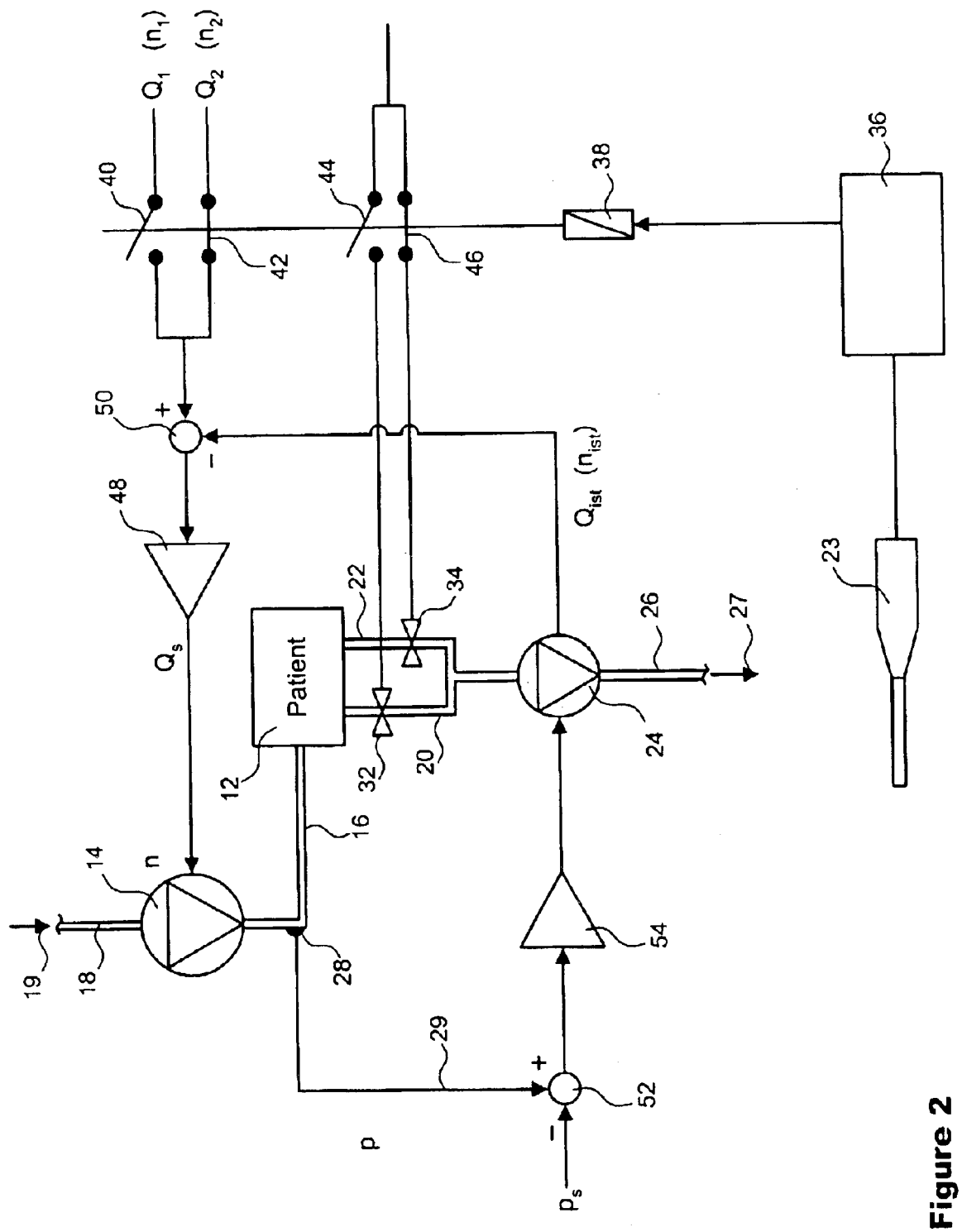
FIG. 2 shows the apparatus in FIG. 1 with further details of the control circuit of the apparatus.

FIG. 2 shows the apparatus 10 together with a schematic representation of a control circuit thereof.

The apparatus 10 is used, for example, for endoscopically irrigating the bladder, the uterus or, when used in arthroscopy, for irrigating a joint, for example the knee.

The apparatus 10 comprises an irrigation pump 14 connected with an irrigation conduit 16 leading to the body cavity 12. The liquid is drawn from a liquid reservoir via a conduit 18 according to an arrow 19.

A first suction conduit 20 leads from the body cavity 12 to a suction pump 24 downstream of the body cavity 12. A second section conduit 22, parallel to the first suction conduit 20, also leads from the body cavity 12 to the suction pump 24. The first suction conduit 20 is connected with an irrigation instrument not shown in detail which can be inserted in the body cavity 12. The second suction conduit 22 is connected with a working instrument 23 schematically shown in FIG. 2, for example a resection instrument, which is used for sucking as well as for carrying out an operation in the body cavity 12, for example for removing tissue.

The liquid along with body liquids like blood, secretions and tissue pieces is drawn from the body cavity 12 by means of the suction pump 24 through the first suction conduit 20 or the second suction conduit 22. The liquid drawn off is drained off via a conduit 26 according to an arrow 27 to a collecting vessel (not shown).

The pressure sensor 28 is associated with the irrigation conduit 16 which is capable of determining the actual pressure p in the irrigation conduit 16 or in the body cavity 12, respectively. The determination of the actual pressure in the body cavity 12 can be done by calculating the actual pressure in the irrigation conduit 16 if the flow resistance of the irrigation conduit 16 is known, for example.

The irrigation pump 14 is a displacement pump and, in the present case, the irrigation pump 14 is a roller pump or a gear pump. A roller pump is described, for example, in the document EP 0 448 909 B1. A roller pump is a peristaltic pump comprising a plurality of rollers arranged on a circular disk rotating about its center axis. When the circular disk rotates, the rollers run along a piece of the tube of the suction conduit 26 and thereby peristaltically change the cross section of this portion of the conduit. A medical gear pump is, for example, described in the document DE 197 25 462 A1 to the same applicants to which herewith is made reference with respect to an exemplary description of the construction and function of a gear pump.

The apparatus 10 comprises a control circuit shown in FIG. 2 which controls the irrigation pump 14 as a function of a predetermined nominal flow rate $Q_s$ which shall prevail in the body cavity 12. The predetermined nominal flow rate $Q_s$ can be adjusted in a simple manner by setting a certain rotational speed n of the irrigation pump 14, in particular in case that the irrigation pump 14 is a roller pump.

The control circuit, however, controls the irrigation pump 14 not only as a function of one predetermined nominal flow rate, but as a function of two nominal flow rates $Q_1$ and $Q_2$, a higher and a lower one, to which two respective rotational speeds $n_1$ (higher nominal flow rate) and $n_2$ (lower nominal flow rate) are associated.

In contrast to that, the suction pump 24 is controlled by the control circuit as a function of a predetermined nominal pressure $p_s$ (broken line 25 in FIG. 1), which shall prevail in the body cavity 12. The suction pump 24 is further controlled by the control circuit as a function of the actual pressure p acquired by the pressure sensor 28 for maintaining the predetermined nominal pressure $p_s$ in the body cavity 12.

The suction pump 24 is a displacement pump too, which is a roller pump in the present case, but can also be a gear pump.

As already mentioned, the irrigation pump 14 is controlled as a function of at least two predetermined nominal flow rates $Q_1$ and $Q_2$ corresponding to two predetermined rotational speeds $n_1$ and $n_2$ of the irrigation pump 14. The control circuit comprises a control unit 36 for the working instrument 23, which automatically switches over between these both nominal flow rates $Q_1$ and $Q_2$ via e.g. a relay 38 and switches 40 and 42 as a function of the operating condition of the already mentioned working instrument 23 connected with the second suction conduit 22. When the working instrument 23, for example a resection instrument, is actuated, the control circuit automatically adjusts the irrigation pump 14 to the higher nominal flow rate $Q_1$ corresponding to the higher rotational speed $n_1$, and upon switching off the working instrument, the control circuit automatically switches over to the lower nominal flow rate $Q_2$ corresponding to the lower rotational speed $n_2$, or vice versa.

In addition, the control circuit also effects the automatic changeover between the suction of the liquid from the body cavity 12 via the first suction conduit 20 or the second suction conduit 22, when the working instrument 23 is switched on so that the liquid, possibly along with body liquids and tissue pieces, is then drawn off via the second suction conduit 22 through the working instrument 23. Valves 32 and 34, for example tube squeezing valves, are provided on the first suction conduit 20 and on the second suction conduit 22 schematically shown in FIG. 1 which are controlled by the control circuit, and which can be closed and opened via switches 44 and 46 connected with the control unit 36 for the working instrument 23, in order to change over between the suction conduits 20 and 22.

With reference to FIG. 2, the control circuit further comprises a controller 48, which is connected, at the input side, with a subtractor or comparator 50, which is supplied, at the input side, with the signal of the respectively set nominal flow rate $Q_1$ or $Q_2$, and also with the signal of the actual rotational speed $n_{ist}$ of the suction pump 24, which corresponds to an actual flow rate $Q_{ist}$, in particular when the suction pump 24 is a roller pump as it is in the shown embodiment. The controller 48 is connected, at the output side, with the irrigation pump 14, and feeds a signal corresponding to the nominal flow rate $Q_s$ thereto.

The pressure sensor 28 further feeds a signal to another subtractor or comparator 52, which signal corresponds to the actual pressure p acquired by the pressure sensor 28. The subtractor or comparator 52 is further connected, at the input side, with a nominal pressure value generator (not shown) feeding a signal corresponding to the nominal pressure $p_s$ to the subtractor or comparator 52. The subtractor or comparator 52 is connected, at the output side, with another controller 54, which is connected, at the output side, with the suction pump 24.

In the following, the control of the apparatus 10 is now described in more detail.

The control of the suction pump 24 for maintaining the nominal pressure $p_s$ in the body cavity 12 as a function of the actual pressure p determined by the pressure sensor 28 (broken lines 29 in FIG. 1) is such that the speed of the suction pump 24 is increased when the actual pressure p exceeds the nominal pressure $p_s$, and the speed of the suction pump 24 is reduced accordingly, when the actual pressure p drops under the nominal pressure $p_s$.

In case that the irrigation pump 14 is a gear pump, the flow rate produced by the irrigation pump 14 is not correlated with the speed of the irrigation pump 14 in a single-valued manner, as it usually is the case with a roller pump. For a gear pump, the flow rate depends on the irrigation pressure in the irrigation conduit 16 as well as on the suction pressure in the suction conduit 20 or 22. For this reason, it is not possible to control the flow rate only by means of the speed of the irrigation pump 14, but a regulation is necessary. Therefore, the control circuit is configured such that the rotational speed $n_{ist}$ of the suction pump 24 is fed back to the irrigation pump 14, i.e. the control circuit uses the speed $n_{ist}$ of the suction pump as a control signal for the actual flow rate. When the liquid unimpededly flows through the body cavity 12 and no liquid enters into the blood stream, i.e. when the flow rate in the irrigation conduit 16 and in the suction conduit 20 or 22 are equal, an independent adjustment of the flow rate and of the pressure is possible without difficulty.

Now, when the nominal flow rate increases from e.g. $Q_2$ to $Q_1$ as a function of which the irrigation pump 14 is controlled as already mentioned, the controller 48 will increase the speed n of the irrigation pump 14, whereby the actual pressure p in the irrigation conduit 16 would increase presently. This would cause the suction pump 24 to increase its speed $n_{ist}$ via the controller 54, in order to reduce the actual pressure p again, and this will be continued as long as the flow rate $Q_1$ in the suction conduit 20 or 22 is adjusted to the newly predetermined flow rate $Q_1$ in the irrigation conduit 16.

On the other hand, if the nominal pressure $p_s$ is increased, the controller 54 would slow down the speed $n_{ist}$ of the suction pump 24 for the time being. This would result in a control deviation for the irrigation pump 14, which, for the time being, increases its speed n, which results in a further increase of the actual pressures, which, in turn, the suction pump 24 tries to compensate by an increase of the suction power. In this way, an increase of the nominal pressure $p_s$ can be obtained without the nominal flow rate $Q_s$ being changed in the end.

When an obstruction, however, occurs in the suction conduit 20 or 22 which would impede the outflow of the liquid from the body cavity 12, another mechanism arises which is caused by the fact that the pressure in the suction conduit 20 or 22 decreases when in general the speed of a roller pump is increased without liquid being able to continue to flow in a sufficient quantity. This results in the pump tube of the roller pump not reaching its complete cross-section in the suction region, i.e. the pump tube partially collapses so that the flow rate does not increase to the same degree or even decreases despite of the increased speed $n_{ist}$ of the suction pump. This effects in turn that the irrigation pump 14, according to the speed $n_{ist}$ of the suction pump 24, which is a measure of the actual flow rate $Q_{ist}$ for the irrigation pump 14, must assume that the actual flow rate $Q_{ist}$ is too high and reduces its speed n accordingly. This results in the desired effect that the pressure in the body cavity 12 is again reduced or not further increased by virtue of the more and more decreasing speed n of the irrigation pump 14.

The afore-mentioned control dependency does not only work when the irrigation pump 14 is a gear pump, but also in case the irrigation pump 14 is a roller pump, although a roller pump does not actually need such a kind of control.

Furthermore, it is possible to determine the loss of liquid in the body cavity 12 by a subtraction of both speeds $n_{ist}$ of the suction pump 24 and the irrigation pump 14, in particular when the irrigation pump 14 as well as the suction pump 24 are roller pumps.

Figure 3:
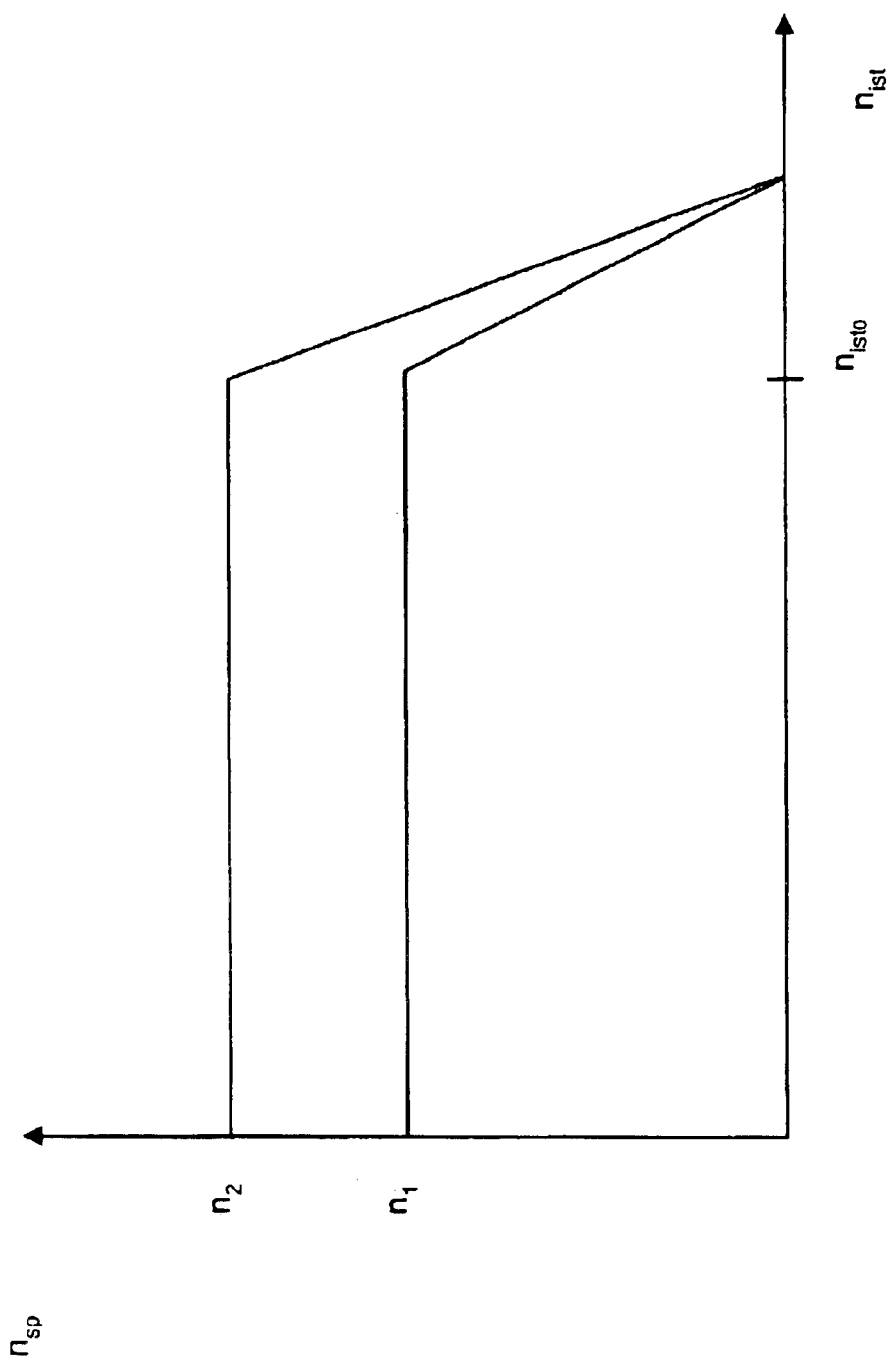
FIG. 3 shows a graph of modified control dependency between the irrigation pump and the suction pump of the apparatus in FIG. 1.

A slightly modified control of the irrigation pump 14 as a function of the suction pump 24 is schematically shown in FIG. 3. In case of an obstruction in the first suction conduit 20 or the second suction conduit 22, the actual pressure p in the body cavity 12 increases, because the irrigation pump 14 further feeds irrigation liquid via the irrigation conduit 16 into the body cavity 12. Since the suction pump 24 is controlled as a function of the predetermined nominal pressure $p_s$, the increase of pressure p in the body cavity 12 results in a higher suction power of the suction pump 24 which is manifested in a higher speed $n_{ist}$ of the suction pump 24. In case of lighter obstructions, the increase of the suction power of the suction pump 24 is sufficient to draw off the obstruction, which is caused, for example, by tissue sticking in the suction conduit 20 or suction conduit 22. In case, however, the removal of the obstruction is not possible, the speed $n_{ist}$ of the suction pump 24 will further increase and exceed a predetermined threshold value $n_{ist0}$. By virtue of the feedback of the speed $n_{ist}$ of the suction pump 24 to the irrigation pump 14, exceeding the predetermined threshold value $n_{ist0}$ of the speed $n_{ist}$ of the suction pump 24 will result in a decreasing speed n, if necessary until the irrigation pump 14 is slowed down to the speed 0.

Another control dependency of the irrigation pump can consist in a control of the irrigation pump as a function of the difference of the speeds of the suction pump and the irrigation pump.

Figure 4:
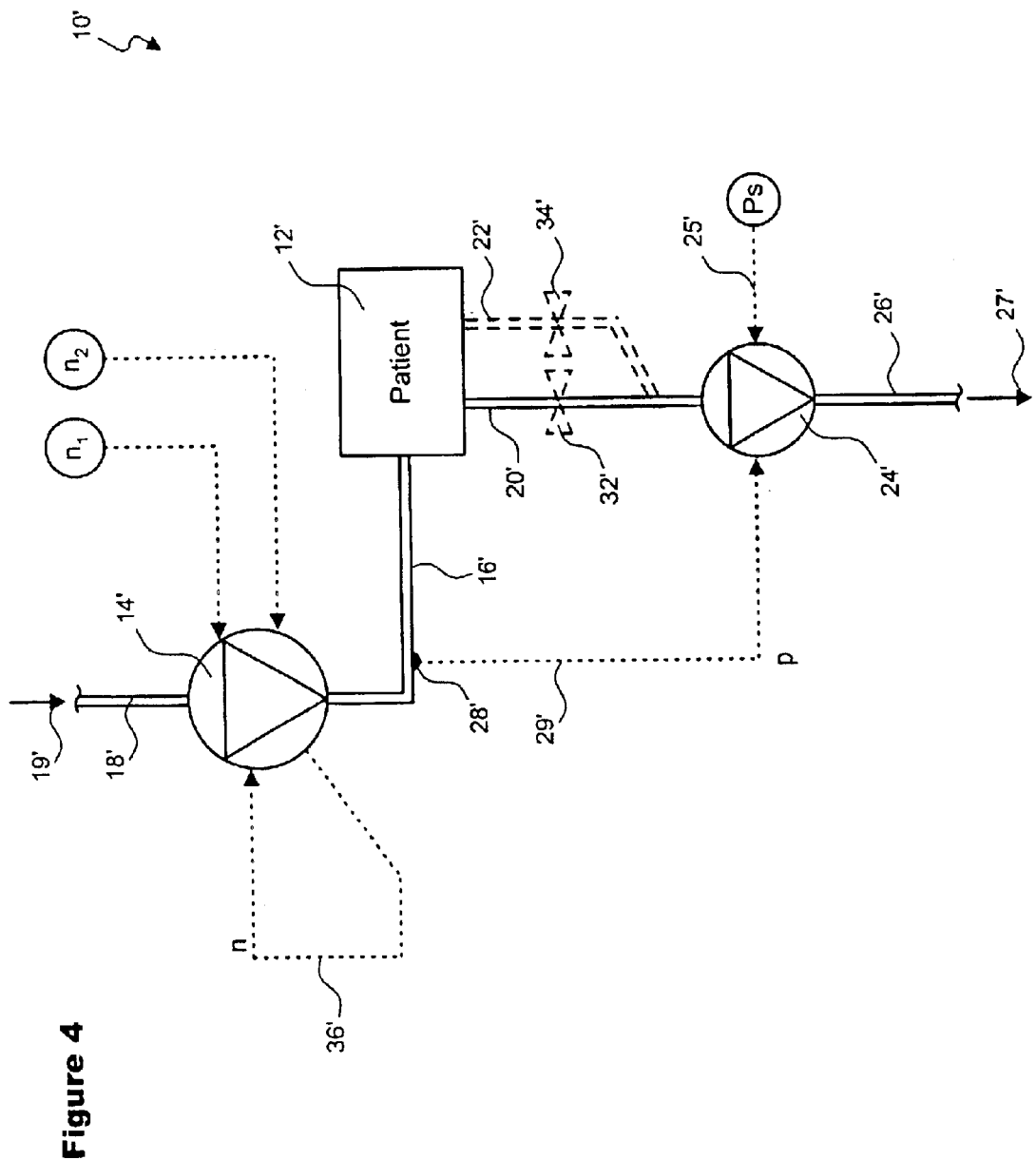
FIG. 4 is a block diagram of an apparatus according to a further exemplary embodiment.

With reference to FIG. 4, there is shown an apparatus 10' for irrigating a body cavity 12' with a liquid, which differs from the apparatus 10' only in that the irrigation pump 14' is not controlled as a function of the suction power of the suction pump 24'. The irrigation pump 14' is rather controlled as a function of the predetermined nominal flow rate or at least two predetermined nominal flow rates corresponding to two predetermined speeds $n_1$ and $n_2$ only so that the predetermined nominal flow rates are maintained in the body cavity 12', as indicated by a broken line 36'. Apart from that, the apparatus 10' does not differ from the apparatus 10 so that reference can be made to the description of the apparatus 10, wherein like components are referenced with the same reference numeral added by a'.

In the afore described embodiment, the irrigation pump 14 or the irrigation pump 14' can be designed as a centrifugal pump instead of a gear pump or, in general, a displacement pump. In case that such a centrifugal pump is used as the irrigation pump, the correlation between the flow rate and the speed of the centrifugal pump is first determined, and the control circuit then uses this correlation in order to adjust or maintain the nominal flow rate.

What is claimed is:

1. An apparatus for irrigating a body cavity with a liquid, comprising an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a nominal pressure and a nominal flow rate, where the control circuit controls the irrigation pump as a function of the nominal flow rate, while it controls the suction pump as a function of the nominal pressure; and wherein the control circuit controls the irrigation pump as a function of the suction power of the suction pump such that the power of the irrigation pump is reduced when the suction power of the suction pump is increased, at least when the suction power of the suction pump exceeds a predetermined threshold value.

2. The apparatus of claim 1, characterized in that a pressure sensor is associated with the irrigation conduit for determining the actual pressure, and the control circuit controls the suction pump as a function of the actual pressure determined by the pressure sensor for maintaining the nominal pressure.

3. The apparatus of claim 1, characterized in that the irrigation pump and the suction pump are displacement pumps.

4. The apparatus of claim 3, characterized in that the irrigation pump is a roller pump or a gear pump.

5. The apparatus of claim 3, characterized in that the suction pump is a roller pump.

6. The apparatus of anyone of claim 1, characterized in that the irrigation pump is a centrifugal pump.

7. The apparatus of claim 1, characterized in that at least two parallel suction conduits lead away from the body cavity, wherein the suction pump is associated with both suction conduits, wherein further one suction conduit is connected with a working instrument, and wherein it can be switched over between both suction conduits as a function of the operating condition of the working instrument.

8. An apparatus for irrigating a body cavity with a liquid, comprising an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a nominal pressure and a nominal flow rate, where the control circuit controls the irrigation pump as a function of the nominal flow rate, while it controls the suction pump as a function of the nominal pressure; and wherein the control circuit uses the speed of the suction pump as a control signal and controls the irrigation pump as a function of said control signal.

9. The apparatus of claim 8, characterized in that the control circuit controls the irrigation pump as a function of the speed of the suction pump, at least when a flow rate threshold value is exceeded, such that the speed of the irrigation pump is reduced when the speed of the suction pump increases.

10. An apparatus for irrigating a body cavity with a liquid, comprising an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a nominal pressure and a nominal flow rate, where the control circuit controls the irrigation pump as a function of the nominal flow rate, while it controls the suction pump as a function of the nominal pressure; and wherein the control circuit controls the irrigation pump as a function of the difference between the speeds of the irrigation pump and the suction pump.

11. The apparatus of claim 10, wherein the irrigation pump and the suction pump are displacement pumps.

12. An apparatus for irrigating a body cavity with a liquid, comprising an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a nominal pressure and a nominal flow rate, where the control circuit controls the irrigation pump as a function of the nominal flow rate, while it controls the suction pump as a function of the nominal pressure; and wherein the control circuit controls the irrigation pump as a function of at least two different nominal flow rates ($Q_1$, $Q_2$).

13. The apparatus of claim 12, characterized in that the control circuit switches over the irrigation pump between the at least two nominal flow rates ($Q_1$, $Q_2$) as a function of the operating condition of a working instrument connected with the control circuit.

14. The apparatus of claim 12, wherein the irrigation pump and the suction pump are displacement pumps.

15. An apparatus for irrigating a body cavity with a liquid, comprising an irrigation pump and, associated therewith, an irrigation conduit leading to the body cavity for feeding the liquid into the body cavity, and at least one suction conduit leading away from the body cavity and, associated therewith, a suction pump for drawing off the liquid from the body cavity, and a control circuit, which controls the irrigation pump and the suction pump such that the liquid passes through the body cavity substantially with a nominal pressure and a nominal flow rate, where the control circuit controls the irrigation pump as a function of the nominal flow rate, while it controls the suction pump as a function of the nominal pressure; and wherein the control circuit determines the difference between the speeds of the suction pump and the irrigation pump.

16. The apparatus of claim 15, wherein the irrigation pump and the suction pump are displacement pumps.

* * * * *